(12) United States Patent
Arishima et al.

(10) Patent No.: US 8,211,990 B2
(45) Date of Patent: Jul. 3, 2012

(54) POLYMERIZABLE COMPOUND, PHOTOCURABLE COMPOSITION, OPTICAL ELEMENT AND OPTICAL HEAD DEVICE

(75) Inventors: Hiroyuki Arishima, Koriyama (JP); Hiroki Hotaka, Koriyama (JP)

(73) Assignee: Asahi Glass Company, Limited, Tokyo (JP)

( * ) Notice: Subject to any disclaimer, the term of this patent is extended or adjusted under 35 U.S.C. 154(b) by 127 days.

(21) Appl. No.: 12/884,302

(22) Filed: Sep. 17, 2010

(65) Prior Publication Data

US 2011/0003957 A1 Jan. 6, 2011

Related U.S. Application Data

(63) Continuation of application No. PCT/JP2009/059094, filed on May 15, 2009.

(30) Foreign Application Priority Data

May 16, 2008 (JP) .................. 2008-130155

(51) Int. Cl.
*G02B 1/00* (2006.01)
*C08F 30/08* (2006.01)

(52) U.S. Cl. ......... 526/279; 359/321; 556/486; 556/489

(58) Field of Classification Search .................. 556/486, 556/489
See application file for complete search history.

(56) References Cited

U.S. PATENT DOCUMENTS

| 4,742,136 | A  | * | 5/1988 | Uchida ................ 526/279 |
| 6,846,897 | B2 | * | 1/2005 | Salamone et al. ....... 528/43 |
| 7,109,262 | B2 | * | 9/2006 | Sapper ................ 524/114 |
| 2003/0158292 | A1 | * | 8/2003 | Masuoka et al. ......... 523/177 |

FOREIGN PATENT DOCUMENTS

| JP | 61-502539 | 11/1986 |
| JP | 10-72569 | 3/1998 |
| JP | 2004-315744 | 11/2004 |
| JP | 2005-298665 | 10/2005 |

OTHER PUBLICATIONS

Saied, Okba et al., Journal of the American Chemical Society, 2005, 127(28), 10008-10009.

* cited by examiner

*Primary Examiner* — Marc Zimmer
(74) *Attorney, Agent, or Firm* — Oblon, Spivak, McClelland, Maier & Neustadt, L.L.P.

(57) ABSTRACT

A compound capable of satisfying both high refractive index and high light resistance, and a photocurable composition containing it, are provided. Further, an optical element having good light resistance against blue laser light, and an optical head device using it, are provided.

A polymerizable compound represented by $SiA^1A^2A^3A^4$ wherein silicon and four cyclic groups are bonded directly or via oxygen. each of $A^1$, $A^2$, $A^3$ and $A^4$ which are independent of one another, is $-(O)_m-X$; and each of four m's which are independent of one another, is 0 or 1. X is preferably a phenyl group. From 0 to 3 hydrogen atoms in the phenyl group are substituted by a polymerizable substituent represented by $CH_2=CR-COO-Y-$, and some or all of remaining hydrogen atoms in the phenyl group may be substituted by a methyl group or a fluorine atom.

10 Claims, 3 Drawing Sheets

POLYMERIZABLE COMPOUND, PHOTOCURABLE COMPOSITION, OPTICAL ELEMENT AND OPTICAL HEAD DEVICE

TECHNICAL FIELD

The present invention relates to a polymerizable compound, a photocurable composition, an optical element and an optical head device.

BACKGROUND ART

High refractive index resin materials are widely used as optical materials, since optical elements may thereby be made to be small-sized or to have high efficiency. Specifically, they are used, for example, for display panels, eyeglass lenses, optical disks or optical filters. In recent years, in such applications, it has been promoted to increase the light intensity or to shorten the wavelength to be used, and accordingly, it has been required to improve light resistance of the high refractive index resin materials. If a resin material inferior in the light resistance is used as a component or an element, a decrease in the transmittance or an increase in the optical strain is likely to occur as the time passes, and it becomes difficult to use it stably over a long period of time.

Such a requirement is particularly distinct in the field of optical disks.

Convexoconcaves so-called pits are formed on the surface of an optical disk such as CD (compact disk) or DVD (digital versatile disk). By an optical head device, it is possible to read out information recorded in pits by irradiating the optical disk with a laser light and detecting its reflected light. In recent years, in order to increase the capacity of an optical disk, it has been promoted to further shorten the wavelength of the laser light and to further reduce the pit size on the optical disk. Specifically, it has been proposed to employ, as a light source, a semiconductor laser which emits a laser light having a wavelength of from 300 to 450 nm (hereinafter referred to also as a blue laser light).

A resin material to be used for such an optical head device, is required to have not only a high refractive index but also high light resistance.

For example, a polarization hologram element to be used as a polarization separation element for an optical head device has a structure wherein a birefringent resin and an isotropic resin are laminated. In order to improve the diffraction efficiency and polarization characteristics of the polarization hologram element, the refractive index in ordinary ray direction or the refractive index in extraordinary ray direction of the birefringent resin is made to be substantially equal to the refractive index of the isotropic resin. However, in the case of a birefringent resin having a high refractive index of at least 1.55, light resistance of the isotropic resin having a high refractive index matching therewith is not sufficient, and there has been a problem that deterioration in the transmittance or aberration occurs. This is because a high refractive index material usually has a large wavelength dispersion of the refractive index, and the absorption for short wavelength light tends to be large.

An example of a conventional high refractive index resin material may be a compound having a skeleton of e.g. fluorene, tetraphenylmethane, 1,1,2,2-tetraphenylethane or biphenyl (Patent Documents 1 and 2). In order to improve the light resistance of such a compound, it is conceivable to increase the number of polymerized groups in its molecule or to add a light stabilizer. However, even by such a method, no adequate light resistance has been obtained, and a further improvement has been desired.

On the other hand, Patent Document 3 discloses a silicon compound. Further, it has been known that a compound having a siloxane bond is a compound having a good light resistance. However, such a material is usually inadequate in the refractive index and thus has had a problem in use for the above-mentioned applications.

PRIOR ART DOCUMENTS

Patent Documents

Patent Document 1: JP-A-2004-315744
Patent Document 2: JP-A-2005-298665
Patent Document 3: JP-A-61-502539

DISCLOSURE OF THE INVENTION

Objects to be Accomplished by the Invention

As indicated above, the high refractive index and the high light resistance tend to oppose to each other. That is, with a compound having a high refractive index, the light resistance tends to be poor, and with a compound having a good light resistance, the refractive index tends to be low. Accordingly, a compound satisfying both high refractive index and high light resistance has not heretofore been found. The present invention has been made from such a viewpoint. That is, it is an object of the present invention to provide a compound which is capable of satisfying both high refractive index and high light resistance, and a photocurable composition containing it.

Further, another object of the present invention is to provide an optical element having good light resistance against blue laser light, and an optical head device using it.

Other objects and merits of the present invention will be made apparent from the following disclosure.

Means to Accomplish the Object

The first embodiment of the present invention relates to a polymerizable compound represented by the following formula (1), wherein silicon and four cyclic groups are bonded directly or via oxygen:

(1)

in the formula (1), each of $A^1$, $A^2$, $A^3$ and $A^4$ which are independent of one another, is $-(O)_m-X$;

each of four m's which are independent of one another, is 0 or 1; and each of four X's which are independent of one another, is any cyclic group selected from a phenyl group, a cyclohexyl group, a cyclohexylphenyl group and a phenylcyclohexyl group; and from 1 to 4 hydrogen atoms in total in cyclic groups in $A^1$ to $A^4$ are substituted by a substituent represented by the following formula (2), and some or all of remaining hydrogen atoms in each of cyclic groups in $A^1$ to $A^4$ may be substituted by a methyl group, a methoxy group, a fluorine atom, a trifluoromethyl group or a trifluoromethoxy group:

$$CH_2=CR-COO-Y- \qquad (2)$$

in the formula (2), R is a hydrogen atom or a methyl group; and

Y is a single bond or an alkylene group; and some or all of hydrogen atoms in the alkylene group may be substituted by a fluorine atom, and the alkylene group may have an oxygen atom in a carbon-carbon bond adjacent thereto or at its terminal bonded to a cyclic group.

In the first embodiment of the present invention, X is preferably a phenyl group which may have a substituent.

In the first embodiment of the present invention, Y is preferably a $C_{2-12}$ alkylene or $C_{2-12}$ alkyleneoxy group, in which some or all of hydrogen atoms may be substituted by a fluorine atom.

In the first embodiment of the present invention, Y is preferably a $C_{2-12}$ alkylene group.

In the first embodiment of the present invention, Y is preferably a $C_{2-12}$ alkyleneoxy group.

In the first embodiment of the present invention, the sum in number of polymerizable moieties represented by the formula (2) in the compound represented by the formula (1) is preferably 1 or 2.

In the first embodiment of the present invention, in each of $A^1$ to $A^4$, it is preferred that the cyclic group is a phenyl group which may have a substituent, and m is 0 (zero).

The second embodiment of the present invention relates to a photocurable composition containing the polymerizable compound in the first embodiment of the present invention.

The third embodiment of the present invention relates to an optical element using a resin material obtained by curing the photocurable composition in the second embodiment of the present invention.

The fourth embodiment of the present invention relates to an optical head device using the optical element in the third embodiment of the present invention.

Advantageous Effects of the Invention

According to the first embodiment of the present invention, it is possible to provide a polymerizable compound which is capable of satisfying both high refractive index and high light resistance.

According to the second embodiment of the present invention, it is possible to obtain a resin material which is capable of satisfying both high refractive index and high light resistance, by curing such a photocurable composition.

According to the third embodiment of the present invention, it is possible to obtain an optical element having good light resistance against blue laser light.

According to the fourth embodiment of the present invention, it is possible to obtain an optical head device suitable for a large capacity.

MODE FOR CARRYING OUT THE INVENTION

As a result of an extensive research, the present inventors have found it possible to obtain a material having both high refractive index and high light resistance, by using a polymerizable compound of silicon derivative represented by the formula (1):

The polymerizable compound represented by the formula (1) has a structure wherein silicon and four cyclic groups are bonded directly or via oxygen. Here, each of $A^1$, $A^2$, $A^3$ and $A^4$ which are independent of one another, is $-(O)_m-X$. Each of four m's which are independent of one another, is 0 or 1. Each of four X's which are independent of one another, is any cyclic group selected from a phenyl group, a cyclohexyl group, a cyclohexylphenyl group and a phenylcyclohexyl group, and from 1 to 4 hydrogen atoms in total in cyclic groups in $A^1$ to $A^4$ are substituted by a substituent represented by the following formula (2), and some or all of remaining hydrogen atoms in each of cyclic groups in $A^1$ to $A^4$ may be substituted by a methyl group, a methoxy group, a fluorine atom, a trifluoromethyl group or a trifluoromethoxy group.

Here, in the present invention, with respect to the phenyl group or the cyclohexyl group at the terminal, in a case where some or all of hydrogen atoms therein are substituted by a methyl group, a methoxy group, a fluorine atom, a trifluoromethyl group or a trifluoromethoxy group, in a normal situation, it should accurately be referred to as a phenylene group or a cyclohexylene group. However, in order to avoid cumbersomeness in referring a non-substituted case and a substituted case separately as e.g. a phenyl group and a phenylene group, even a case where a phenyl group or a cyclohexyl group has a substituent, it is referred to simply as a phenyl group or a cyclohexyl group.

$$CH_2=CR-COO-Y- \qquad (2)$$

In the formula (2), R is a hydrogen atom or a methyl group. Y is a single bond or a $C_{1-12}$ alkylene group, and some or all of hydrogen atoms in the alkylene group may be substituted by a fluorine atom, and the alkylene group may have an oxygen atom in a carbon-carbon bond adjacent thereto or at its terminal bonded to a cyclic group. Further, in a case where a plurality of substituents of the formula (2) are present, the above R and Y may, respectively, be the same or different within the above defined respective ranges. The sum in number of polymerizable moieties represented by the formula (2) in the compound represented by the formula (1) is at least 1 for polymerization. Specifically, it is preferably from 1 to 4, particularly preferably 1 or 2.

The polymerizable compound of the present invention is preferably one having a structure represented by the following formula (3). That is, in the formula (1), X is preferably a phenyl group. In substituents $Z_1$ to $Z_4$ in four phenyl groups in the formula (3), each of a, b, c and d which are independent of one another, is from 0 to 3, and their sum (a+b+c+d) is from 1 to 4. Some or all of remaining hydrogen atoms in the phenyl groups may be substituted by a methyl group, a methoxy group, a fluorine atom, a trifluoromethyl group or a trifluoromethoxy group. Each of i, j, k and l which are independent of one another, is 0 or 1.

(3)

In the formula (2), Y is preferably a $C_{2-12}$ alkylene or $C_{2-12}$ alkyleneoxy group, in which some or all of hydrogen atoms may be substituted by a fluorine atom. Particularly, it is preferably a $C_{2-12}$ alkylene group. Otherwise, it is preferably a $C_{2-12}$ alkyleneoxy group. Especially, Y is preferably a $C_{2-6}$ alkyleneoxy group, since a high refractive index can thereby be easily obtained. Further, it is preferred that the sum in number of substituents represented by the formula (2) in $A^1$, $A^2$, $A^3$ and $A^4$ is 1 or 2.

In the formula (1), in each of $A^1$ to $A^4$, it is preferred that the cyclic group is a phenyl group which may have a substituent, and m is 0 (zero), whereby the light resistance becomes high.

Now, embodiments of the present invention will be described in detail.

Embodiment 1

The polymerizable compound in this embodiment has a structure represented by the formula (3), i.e. a structure wherein silicon and four phenylene groups are bonded directly or via oxygen. Here, $Z_1$ to $Z_4$ are substituents represented by the following formula (4):

$$CH_2=CR-COO-Y^1- \quad (4)$$

In the formula (4), R is a hydrogen atom or a methyl group. $Y^1$ is a single bond or either an alkylene group represented by $C_pH_{2p}$ (wherein p is an integer of from 1 to 12), an alkyleneoxy group represented by $C_qH_{2q}O$ (wherein q is an integer of from 1 to 12), a group containing, as a repeating unit, an ethyleneoxy group represented by $(CH_2CH_2O)_r$ (wherein r is an integer of from 1 to 6), or a group containing, as a repeating unit, a propyleneoxy group represented by $(CH_2CH(CH_3)O)_s$ (wherein s is an integer of from 1 to 4).

A resin material obtainable by polymerizing a photocurable composition (which may be referred also as a composition) containing the polymerizable compound of the formula (3) has a high refractive index and at the same time is excellent in light resistance. Accordingly, such a resin material can be used suitably for an optical element which is required to have high light resistance against blue laser light. Now, the compound of the formula (3) will be described in further detail.

The polymerizable compound in this embodiment is a (meth)acrylate compound having a skeleton wherein silicon and four phenyl groups are bonded directly or via oxygen.

Here, the phenyl groups bonded to the silicon site show excellent light resistance in a visible wavelength range of from 400 nm to 800 nm. Further, such phenyl groups are functional groups with high polarizability which contributes also to a high refractive index. As the number of phenyl groups increases, the refractive index can be made high.

Accordingly, in the present invention, the maximum number of phenyl groups which can be bonded to the silicon site i.e. four phenyl groups are introduced. Here, to at least one of the four phenyl groups, a substituent having a polymerizable site is connected, and the terminal end of such a site has a (meth) acryloyloxy group as a polymerizable functional group.

At least one polymerizable site may be connected.

In the present invention, the phenyl groups may be bonded to silicon via oxygen. In such a case, each of i, j, k and l in the formula (3), which are independent of one another, is 0 or 1. However, when oxygen is interposed, the refractive index of a resin material obtainable by polymerizing such a composition tends to be low. Further, the light resistance is better when no oxygen is interposed. Accordingly, it is preferred that the phenyl groups are bonded to silicon without interposition of oxygen. That is, i, j, k and l in the formula (3) are preferably all 0 (zero).

In the formula (3), each of a, b, c and d which are independent of one another is an integer of from 0 to 3, provided that at least one of them is at least 1, so that they are not zero at the same time. When the crosslink density becomes high, the light resistance may sometimes be improved. Accordingly, at least two among a, b, c and d are preferably at least 1. However, if the number of $Z_1$, $Z_2$, $Z_3$ and $Z_4$ as polymerizable groups is too large, the density of phenyl groups decreases, and the refractive index also decreases. Therefore, the sum of a, b, c and d is preferably at most 4, more preferably 1 or 2.

In the present invention, some or all of hydrogen atoms in each phenyl group may be substituted by a methyl group, a methoxy group, a fluorine atom, a trifluoromethyl group or a trifluoromethoxy group. For example, since the transmittance in a ultraviolet wavelength region can be made high, it may be substituted by a fluorine atom, a trifluoromethyl group or a trifluoromethoxy group, and since the melting point can be made low, it may be substituted by a methyl group or a methoxy group. Such substitution may variously be selected depending upon the particular purpose. However, the refractive index decreases by the substitution, and therefore, in order to obtain a high refractive index, hydrogen atoms are preferred.

In the formula (4), R is a hydrogen atom or a methyl group. Accordingly, the polymerizable group in the formula (4) is an acryloyloxy group or a methacryloyloxy group. The (meth) acryloyloxy group is susceptible to a photopolymerization reaction and is excellent in the productivity, since the curing time is short.

Further, it can be stabilized by using a known stabilizer such as a phenol type antioxidant or a hindered amine type photostabilizer, and a useful stabilizer is not limited very much. Accordingly, by using a (meth)acryloyloxy group as the polymerizable group, it is possible to further improve light resistance by utilizing a stabilizer. Further, since the polymerization rate is high, it is preferred to employ an acryloyloxy group as the polymerizable group. That is, in the formula (4), R is preferably a hydrogen atom.

As mentioned above, each of $Z_1$, $Z_2$, $Z_3$ and $Z_4$ in the formula (3) which are independent of one another, is a substituent having a polymerizable site, represented by the formula (4).

$Y^1$ in the formula (4) is a single bond or any one of an alkylene group represented by $C_pH_{2p}$, an alkyleneoxy group represented by $C_qH_{2q}O$, a group containing, as a repeating unit, an ethyleneoxy group represented by $(CH_2CH_2O)_r$ and a group containing, as a repeating unit, a propyleneoxy group represented by $(CH_2CH(CH_3)O)_s$. Here, p is an integer of from 1 to 12, q is an integer of from 1 to 12, r is an integer of from 1 to 6, and s is an integer of from 1 to 4.

The above alkylene and alkyleneoxy groups may be linear or branched, but are preferably linear, since controllability of the refractive index will thereby be excellent. Further, if the numerical values of p, q, r and s are small, the polymerization reaction tends to hardly proceed, and if they are too large, the refractive index tends to be small. Therefore, it is preferred that p is from 3 to 6, q is from 2 to 5, and each of r and s is 1 or 2. A linear alkylene or alkyleneoxy group is preferred, whereby controllability of the refractive index will be excellent, and the synthesis will be simple. It is preferred to select an alkylene group in order to avoid deterioration of light resistance by an increase of the absorption coefficient or extension of the absorbance towards the long wavelength side, by bonding of the phenyl group and the alkyleneoxy group. Here, in order to adjust the refractive index or the wavelength dispersion of the refractive index, some or all of hydrogen atoms in the group may be substituted by a halogen atom, a phenyl group or a cyclohexyl group. However, from the viewpoint of the high refractive index and high light resistance, it is preferred to maintain hydrogen atoms without substitution. However, in a case where among halogen atoms, fluorine atoms are used for substitution, a material having a sharp wavelength distribution in a low refractive index region, i.e. a material having a low Abbe number may be obtainable, and accordingly, fluorine atoms may suitably be introduced in order to adjust the wavelength dispersion property.

By using the polymerizable compound in this embodiment, it is possible to obtain a resin material having both high refractive index and high light resistance.

Embodiment 2

The present invention provides a composition containing the above-described polymerizable compound (hereinafter referred to also as a photocurable composition). The polymerizable compound contained in this composition may be a single compound of the formula (1) or a plurality of such compounds. The compound of the formula (3) described in the first embodiment 1 may be used particularly preferably. Further, the composition in this embodiment may contain a polymerizable compound other than the formula (1).

The polymerizable compound other than the formula (1) may be suitably selected for use depending upon the purpose of adjusting e.g. the melting point, viscosity or refractive index, and is not particularly limited. The proportion of the compound of the formula (1) contained in the polymerizable compound in the composition is preferably at least 10 mol %, more preferably at least 30 mol %, particular preferably at least 50 mol %. It is thereby possible to obtain a resin which has a high refractive index and is excellent also in light resistance.

The composition in this embodiment may contain a reaction initiator to be used for the polymerization reaction. Here, as the polymerization reaction, a photopolymerization reaction or a thermal polymerization reaction may, for example, be mentioned. However, a photopolymerization reaction is preferred, whereby it is not required to consider thermal influences over peripheral components. Light rays to be used for the photopolymerization reaction may, for example, be ultraviolet rays or visible light rays, but ultraviolet rays are preferred, since the polymerization rate is thereby high.

As a photopolymerization initiator, a known material may be employed. For example, one or more selected from the group consisting of acetophenones, benzophenones, benzoins, benzyls, Michler's ketones, benzoin alkyl ethers and benzyl methyl ketals may suitably be selected for use. The amount of the photopolymerization initiator is preferably from 0.1 mass % to 5 mass %, particular preferably from 0.3 mass % to 2 mass %, based on the total amount of the composition.

Other components which may be incorporated to the composition in this embodiment may, for example, be ultraviolet absorbers, antioxidants and stabilizers such as light stabilizers. The amount of such other components is preferably at most 5 mass %, particularly preferably at most 2 mass %, based on the total amount of the composition.

In the composition in this embodiment, an organic solvent may be contained. However, for the purpose of dilution, it is preferred to employ a low viscosity polymerizable compound rather than an organic solvent. Further, in order to facilitate the handling, it is preferred to use the composition by heating it to lower the viscosity within a range not to let it undergo thermal polymerization.

As described in the foregoing, by curing the composition containing the polymerizable compound of the present invention, it is possible to obtain a resin material having both high refractive index and high light resistance.

Embodiment 3

The present invention provides an optical element using a resin material obtained by curing the composition as described in the Embodiment 2. The optical element may be used not only as an element utilizing the high refractive index but also for various diffraction elements by utilizing the large wavelength dispersion of the refractive index.

For example, in a polarization hologram element disclosed in JP-A-11-211905, an optically isotropic medium is required which has a refractive index matching with either an ordinary light refractive index or an extraordinary light refractive index of polymer liquid crystal having a convex or concave shape, and as such an isotropic medium, the resin material of the present invention may be employed.

Further, in a wavelength selective polarization hologram element as disclosed in JP-A-2005-209327, the resin material of the present invention may be employed as an optically isotropic medium matching with either a left or right circularly-polarized light among the refractive index wavelength dispersion against a circularly-polarized light of cholesteric polymer liquid crystal having a convex or concave shape. Further, the resin material of the present invention may be likewise used as an optically isotropic medium also in a diffraction element of a non-polarized system without being limited to a polarized element. Particularly, as described hereinafter, the resin material of the present invention may be used also as a wavelength-selective diffraction element to be used in a non-polarized system.

The resin material of the present invention has high light resistance, and accordingly, it is useful as stabilized over a long period of time in an optical system employing blue laser light, without a decrease in transmittance or without an increase in optical strain as the time passes.

As a method for preparing the optical element, it is possible to employ a method which has been commonly used heretofore, but a photocuring type imprint may be used which has attracted attention in recent years. Further, the above resin material is useful also as an adhesive to laminate optical elements one another.

Now, a case wherein the resin material obtained by the present invention is applied to a wavelength-selective diffraction grating in a non-polarized system, will be described.

Figure 1:
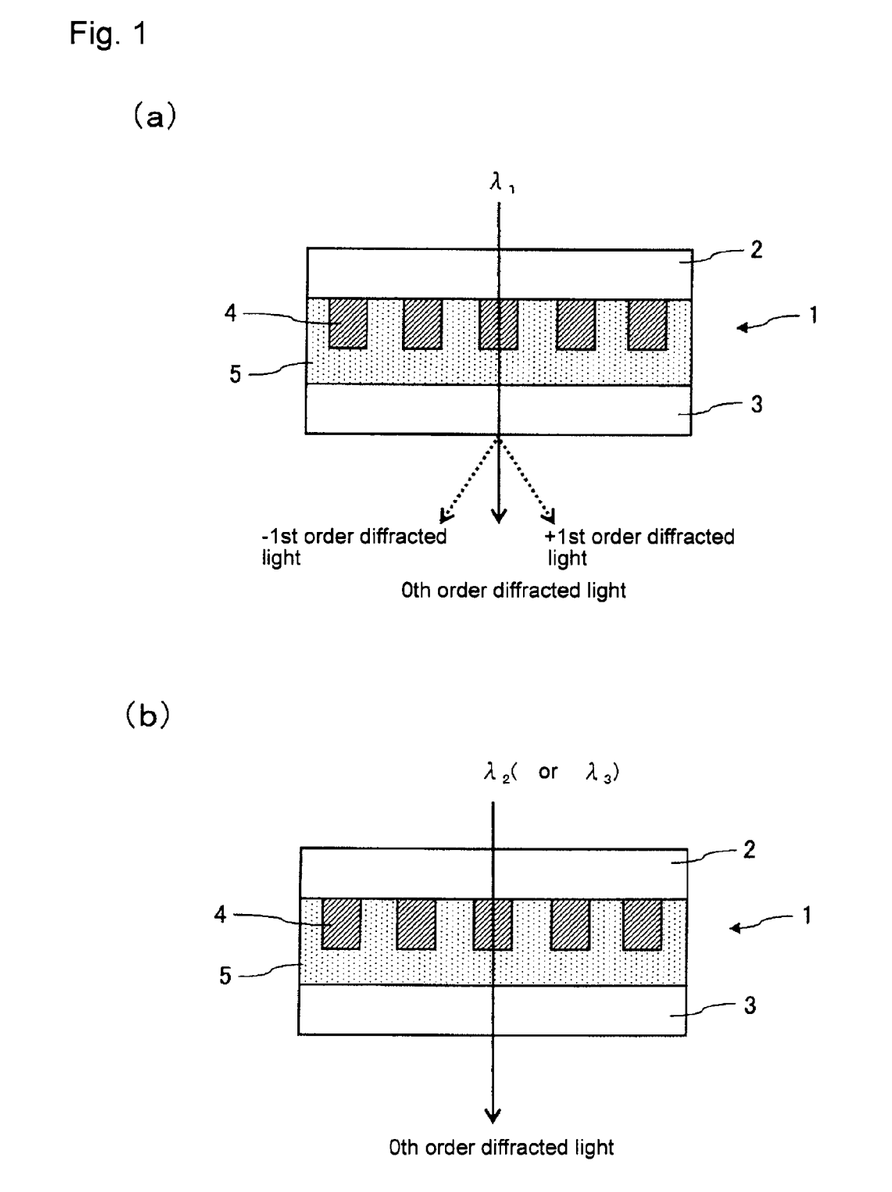
FIG. 1 is a schematic cross-sectional view of a wavelength-selective diffraction grating in an embodiment of the present invention.

FIG. 1 is a schematic cross-sectional view of a wavelength-selective diffraction grating in this embodiment. FIG. 1(a)

shows a state in which incident light with wavelength $\lambda_1$ is diffracted, and FIG. 1(b) shows a state in which incident light with wavelength $\lambda_2$ or $\lambda_3$ is transmitted.

The wavelength-selective diffraction grating 1 comprises a pair of transparent substrates 2 and 3, a convexoconcave section 4 formed on the transparent substrate 2 and having periodical convexoconcave shapes in its cross section, and a filling section 5 to fill at least concave portions of the convexoconcave section 4. The convexoconcave section 4 and the filling section 5 are, respectively, formed by curing the compositions of the present invention. In the example in FIG. 1, the convexoconcave section 4 is constituted solely by convex shapes, and the filling section 5 is constituted by convexoconcave shapes. However, both of them may be made of convex shapes, so that they are disposed adjacent to each other. Otherwise, both of them may be constituted by convexoconcave shapes so that they are disposed to face each other. Here, it is preferred that at least the filling portion to be formed later, is made to have convexoconcave shapes as shown in FIG. 1, also from the viewpoint of the adhesion of the transparent substrates 2 and 3.

As the transparent substrates 2 and 3, plastic substrates made of e.g. an acrylic resin or glass substrates may, for example, be used. With a view to securing the reliability, it is preferred to employ glass substrates. The surface shape of the transparent substrates 2 and 3 is preferably a flat surface when mass production is taken into consideration, but may have a curved surface like a plastic lens. Further, an anti-reflection film or the like may be formed on the surface of the transparent substrates 2 and 3.

The convexoconcave section 4 and the filling section 5 are, respectively, constituted by optically isotropic materials, for which resin materials obtained by curing the compositions of the present invention can be used. The convexoconcave section 4 has a shape of e.g. binary type, blazed type or pseudo blazed type having the blazed type approximated in a stair case pattern, and it is formed by a photolithography method, a 2P method employing a metal die or glass die, imprinting or injection molding.

Otherwise, by using a transparent substrate having a convexoconcave section formed by processing an inner surface side of at least one transparent substrate into convexoconcave shapes by etching or pressing, the photocurable composition of the present invention is filled and cured in the convexoconcave section to form a filling section.

Further, the filling section may be constructed by forming a convexoconcave section on each of the transparent substrates 2 and 3 and filling and curing the photocurable composition of the present invention between the convexoconcave sections of the two substrates. By adopting this construction, the product is obtained in such a state where two diffraction gratings are laminated, whereby it is possible to obtain different diffraction characteristics for every wavelength to be used.

Figure 3:
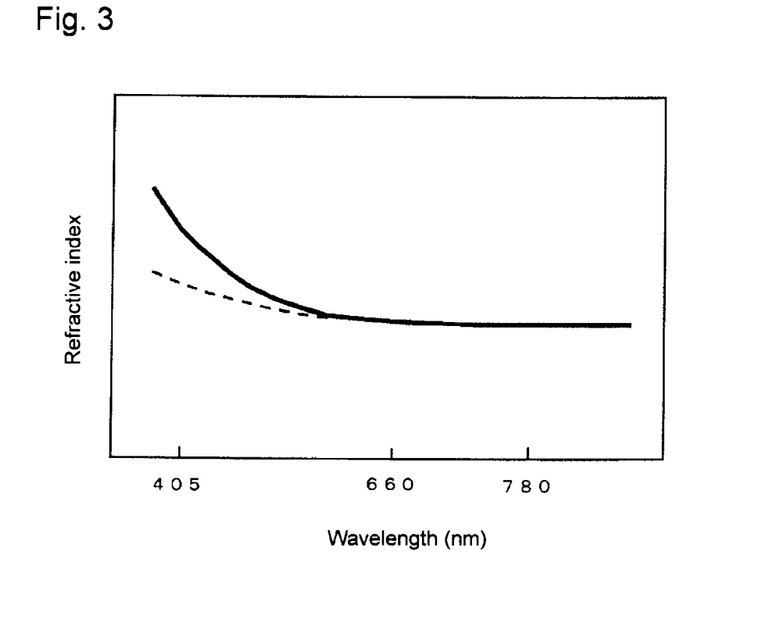
FIG. 3 is a graph showing a wavelength dispersion of a material to be used in the present invention.

As one of preferred modes, the materials to be used for the convexoconcave section 4 and the filling section 5 are selected so that they are different in the wavelength dispersion property of the refractive index, as shown in FIG. 3. It is thereby possible to prepare a wavelength-selective diffraction grating. For example, two types of materials to be used for the convexoconcave section 4 and the filling section 5 have the wavelength dispersion properties of the refractive indices, respectively, as shown in FIG. 3 (represented by a solid line and a dotted line).

Here, in FIG. 3 and in FIG. 4 which will be described hereinafter, the solid line represents the refractive index of a material having a relatively large wavelength dispersion, and the dotted line represents the refractive index of a material having a relatively small wavelength dispersion. This diffraction grating may be constructed by using a material represented by such a solid line and a material represented by such a dotted line for the convexoconcave section 4 and the filling section 5, respectively. The material of the present invention can be used as either material depending upon the materials to be used in combination.

In the case of FIG. 3, there is a difference in the refractive index between the convexoconcave section 4 and the filling section 5 to incident light with wavelength $\lambda_1$=405 nm, whereby diffraction occurs. However, the refractive indices are substantially the same to incident light with wavelength $\lambda_2$=660 nm or $\lambda_3$=780 nm, whereby the light will be transmitted without being diffracted.

The wavelength dispersibility of the refractive index is not limited to the example in FIG. 3. The relation of the wavelength dispersions of the refractive indices of the two types of materials to be used for the convexoconcave section 4 and the filling section 5 may suitably be selected depending upon the particular purpose. For example, by utilizing the relation as shown in FIG. 4, it is possible to prepare an optical element whereby incident light with wavelength $\lambda_1$=405 nm will be transmitted, while diffraction takes place against incident light with wavelength $\lambda_2$=660 nm or $\lambda_3$=780 nm.

Figure 4:
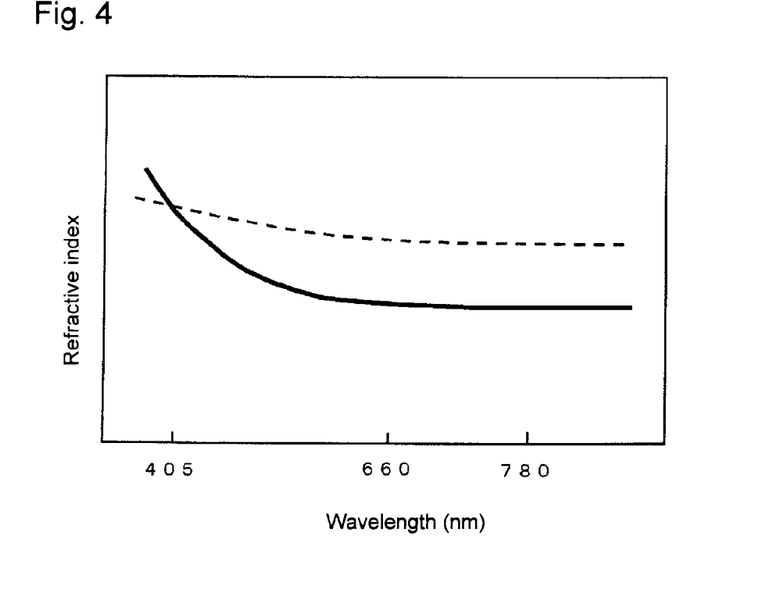
FIG. 4 is a graph showing another wavelength dispersion of a material to be used in the present invention.

Of course, the materials of the present invention may be used not only for a case shown in FIG. 3 or FIG. 4 but also in such a case where when formed into a diffraction grating, they show gradual differences in the refractive index with at least three wavelengths. Further, a material having birefringence such as liquid crystal, may be used as another material constituting the diffraction grating, and the wavelength at which the refractive indices match each other may be selected freely including the presence or absence in the visible light region.

The wavelength-selective diffraction grating 1 may, for example, be prepared as follows. Here, as resin materials constituting the convexoconcave section 4 and the filling section 5 and having the above-mentioned respective optical characteristics, a first photocurable composition and a second photocurable composition by the present invention are employed.

The resin material by the present invention is a material having a large wavelength dispersibility, and accordingly, in FIG. 3 or 4, it can be suitably used as a material having a larger wavelength dispersibility. At that time, a material having a small wavelength dispersibility may suitably be selected for use, and for example, a resin containing sulfur can be selected. However, in a case where a material having a larger wavelength dispersibility, such as a resin having fine particles of metal oxide dispersed therein, is used, the resin material by the present invention may have a relatively small wavelength dispersibility. Accordingly, the degree of the wavelength dispersion may be selected by a particular combination of the materials to be used.

In the following, a case will be described in which the composition by the present invention is employed for the convexoconcave section.

Firstly, on a transparent substrate 2 made of a glass substrate, the first photocurable composition of the present invention is applied by a spin coating method. Then, the photocurable composition is cured by irradiation with ultraviolet rays, followed by processing into a grating form by a dry etching method to form a convexoconcave section 4.

Then, the second photocurable composition of the present invention is applied on the convexoconcave section 4 to fill at least concaves of the convexoconcave section 4. At that time, it is easy for the production to cover the entire surface of the convexoconcave section 4. Then, a transparent substrate 3 made of a glass substrate is laminated thereon. Otherwise, before filling the second photocurable composition, a cell may be formed by overlaying the transparent substrate 3 on the transparent substrate 2 having the convexoconcave section 4 provided thereon and having a sealing material provided along the periphery, and the second photocurable composition may be injected and filled into the space in the cell.

Then, the second photocurable composition is polymerized under irradiation with ultraviolet rays to form a filling section 5. In this manner, a wavelength-selective diffraction grating 1 can be obtained.

By using the photocurable composition of the present invention, it is possible to form a convexoconcave section 4 or a filling section 5, having a high diffractive index and high light resistance. It is thereby possible to increase the durability against blue laser light, whereby stable use of the wavelength-selective diffraction grating 1 over a long period of time becomes possible by suppressing a decrease in the transmittance or an increase in the optical strain as the time passes.

Further, the photocurable composition of the present invention is useful also for optical elements having other constructions. Specifically, a hologram diffraction grating to focus or disperse light by a curved pattern, an aberration-correcting element having a concentric diffraction pattern, or a wavelength-selective diffraction grating may, for example, be mentioned. Here, the diffraction pattern may be provided at a part of a light transmission region, and for example, an aperture-limiting element provided only along the outer circumference may, for example, be included. Such an optical element may be set, for example, between an object lens and a collimator lens, but not limited thereto.

Embodiment 4

In the Embodiment 3, it has been described that a composition containing the polymerizable compound of the present invention is cured, and by using the obtained resin material, an optical element is prepared. Such an optical element is useful for an optical head device to record information on an optical recording medium and/or to reproduce the information recorded on the optical recording medium. It is particularly useful for an optical head device for an optical information-recording and reproducing device employing blue laser light like BD (blue-ray disk), the practical use of which has started recently. Specifically, it is preferably disposed in a light path of laser light of an optical head device. Further, it is preferably used also in other applications where a high refractive index and high light resistance are required.

Now, an optical head device in this embodiment will be described.

Figure 2:
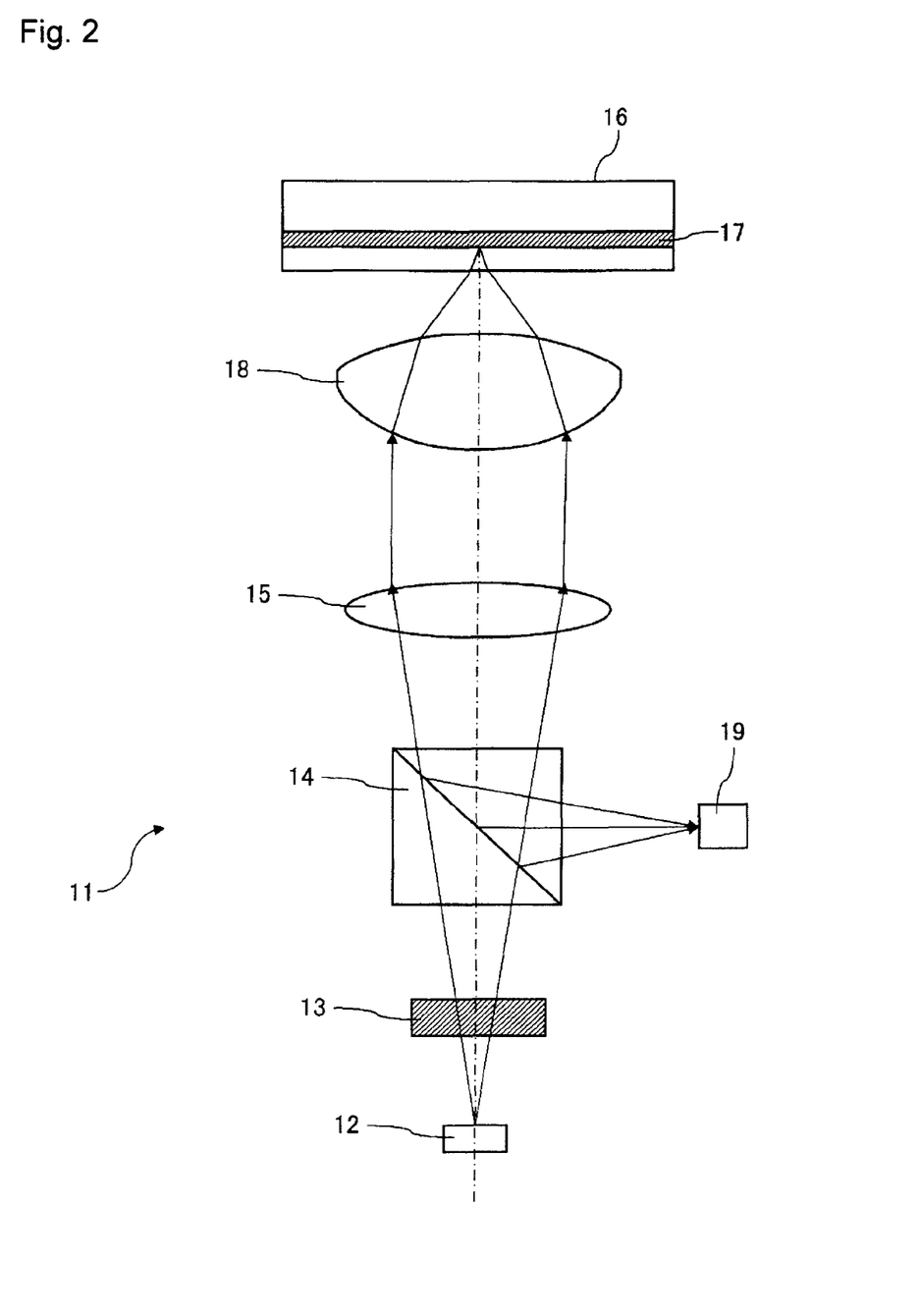
FIG. 2 is a block diagram of an optical head device in an embodiment of the present invention.

FIG. 2 is a block diagram of the optical head device in this embodiment. As shown in this Fig., an optical head device 11 comprises a light source 12 to emit laser light, a wavelength-selective diffraction grating 13, a beam splitter 14 to let the laser light transmit, a collimator lens 15 to make the laser light to be parallel, an object lens 18 to focus the light to a recording layer 17 of an optical disk 16, and a light detector 19 to detect a reflected light from the optical disk 16. The optical head device 11 employs three beams in tracking control at the time of reading out information recorded on e.g. BD. The wavelength-selective diffraction grating 13 is a three beams-generating diffraction grating, to which the element described in the Embodiment 3 (the wavelength-selective diffraction grating 1 in FIG. 1) is applied.

In FIG. 2, the wavelength-selective diffraction grating 13 is provided between the light source 12 and the beam splitter 14. However, the wavelength-selective diffraction grating 13 may be provided between the beam splitter 14 and the object lens 18, so long as the construction is such that the wavelength-selective diffraction grating 13 is provided in the light path between the light source 12 and the object lens 18. Here, it is preferred to dispose the wavelength-selective diffraction grating 13 between the light source 12 and the beam splitter 14 as shown in FIG. 2, whereby the reflected light from the optical disk can be led to the light detector 19 without being diffracted by the wavelength-selective diffraction grating 13, and the efficiency for utilization of light will be high.

The light source 12 may, for example, be constituted by a semiconductor laser diode and designed to form laser light with a wavelength to meet the type of the optical disk 16 and emit it to the wavelength-selective diffraction grating 13. As the light source 12, a usual laser light source which is commonly used in an optical head device, may be used. Specifically, a semiconductor laser is suitable, but another laser may be used. The resin material obtainable by the present invention has good light resistance against blue laser light, and accordingly, by using blue laser as the light source, it is possible to increase the capacity of the optical head device.

In this embodiment, the wavelengths of laser lights are set to be, for example, 405 nm (wavelength $\lambda_1$) and 660 nm (wavelength $\lambda_2$). Further, a plurality of light sources emitting laser lights with wavelengths different from one another may be provided, so that from each light source, laser light is emitted to the wavelength-selective diffraction grating 13.

The wavelength-selective diffraction grating 13 outputs to the beam splitter 14 three beams including light (0th order diffracted light) having laser light with wavelength $\lambda_1$ transmitted without being diffracted, and lights (±1st order diffracted lights) having laser light with wavelength $\lambda_1$ diffracted. Further, the wavelength-selective diffraction grating 13 transmits laser light with wavelength $\lambda_2$ and outputs it to the beam splitter 14.

The beam splitter 14 is constituted by a transparent material such as glass or plastic and provided with a reflection surface to reflect the reflected light from the optical disk 16.

The collimator lens 15 is also constituted by a transparent material such as glass or plastic and designed to make incoming laser light to be parallel.

The object lens 18 has a predetermined numerical aperture NA and designed to focus incident light from the collimator lens 15 on a recording layer 17 in the optical disk 16 and to capture reflected light from the recording layer 17.

The light detector 19 comprises a lens, a photodiode, etc. and designed to convert reflected light from the optical disk 16, reflected by the reflection surface of the beam splitter 14, to an electric signal. Further, the light detector 19 receives reflected lights of three beams with wavelength $\lambda_1$, a main beam formed by the 0th order diffracted light and two sub-beams formed by the ±1st order diffracted lights, detects a tracking error based on the difference in quantity of light between the two sub-beams and outputs the detected information to a tracking control section (not shown).

In a case where the optical disk 16 is BD, the optical head device 11 operates as follows.

Firstly, with respect to light with wavelength $\lambda_1$ emitted from the light source 12, a part of the emitted light is diffracted by the wavelength-selective diffraction grating 13, whereby from the wavelength-selective diffraction grating 13, lights including 0th order diffracted light and ±1st order diffracted lights are emitted and transmitted through the beam splitter 14 and made to be parallel by the collimator lens 15.

The parallel lights emitted from the collimator lens 15 are focused by the object lens 18 in the form of three beams consisting of 0th order diffracted light and ±1st order diffracted lights, on the information recording track of the optical disk 16. Then, lights reflected by the optical disk 16 are again transmitted from the object lens 18 through the collimator 15 and reflected by the beam splitter 14, whereupon the main beam formed by the 0th order diffracted light and the two sub-beams formed by the ±1st order diffracted lights, are focused on the receiving surface of the light detector 19. And, by the light detector 19, a tracking error signal is detected based on the difference in quantity of light between the two sub-beams and output to the tracking control section (not shown).

In a case where the optical disk 16 is DVD, the optical head device 11 operates as follows.

Firstly, light with wavelength $\lambda_2$ emitted from the light source 12 is transmitted without being diffracted by the wavelength-selective diffraction grating 13 and then transmitted further through the beam splitter 14 and is made to be parallel by the collimator lens 15. Then, this parallel light is focused by the object lens 18 on the information recording track of the optical disk 16. And, light reflected by the optical disk 16 is again transmitted through the object lens 18 and the collimator lens 15, reflected by the beam splitter 14 and then focused on the receiving surface of the light detector 19.

As described in the foregoing, by using an optical element obtained by curing the composition containing the polymerizable compound of the present invention, it is possible to prepare an optical head device suitable for a large capacity. It should be mentioned that the present invention is not limited to the above-described embodiments, and various modifications may be made within a range not to depart from the concept of the present invention.

EXAMPLES

Now, the present invention will be described in detail with reference to Examples and Comparative Examples, but the present invention is by no means limited to the following Examples.

<Preparation of Polymerizable Compounds>

Example 1

Compound A was prepared via compounds A-1, A-2 and A-3, in accordance with the following methods.

In the above formulae, TIPS represents a triisopropylsilyl group.

(a) Preparation of Compound A-1

To 300 mL of tetrahydrofuran (hereinafter referred to as THF), 7.0 g (40 mmol) of 4-bromophenol and 6.7 mL (49 mmol) of triethylamine were dissolved and stirred, and then, 10.3 mL (49 mmol) of triisopropylsilyl chloride (TIPS-Cl) was slowly dropwise added over a period of 10 minutes and reacted at room temperature for 12 hours. Then, water and ethyl acetate were added, and the organic layer was extracted. Further, the organic layer was sufficiently dried by adding magnesium sulfate, and then the solvent was distilled off. By using ethyl acetate and hexane (volume ratio of 1:19), purification by column chromatography was carried out to obtain 12.1 g of colorless transparent compound A-1. The yield was 92%.

(b) Preparation of Compound A-2

To 100 mL of THF, 5.0 g (15 mmol) of compound A-1 was dissolved, followed by stirring at −30° C. in a nitrogen atmosphere. Then, 5.9 mL (15 mmol) of a n-butyllithium hexane solution having a concentration of 2.6 mol/L was slowly dropwise added over a period of about 5 minutes. After a reaction at −30° C. for 20 minutes, 4.5 g (15 mmol) of triphenylchlorosilane dissolved in 50 mL of THF was slowly dropwise added over a period of about 5 minutes. Then, after maintaining the system at −30° C. for 15 minutes, a reaction was carried out at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:19), to obtain 4.0 g of white solid compound A-2. The yield was 52%.

(c) Preparation of Compound A-3

To 100 mL of THF, 3.0 g (5.9 mmol) of compound A-2 and 1.7 g (6.5 mmol) of tetrabutylammonium fluoride (TBAF) were dissolved and stirred at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:3), to obtain 1.3 g of white solid compound A-3 The yield was 63%.

(d) Preparation of Compound A

To 100 mL of THF, 1.3 g (3.7 mmol) of compound A-3, 1.1 g (4.1 mmol) of triphenylphosphine and 0.59 g (4.1 mmol) of 2-hydroxyethyl acrylate were dissolved and stirred, and while cooling by an ice bath in a nitrogen atmosphere, 1.8 g (4.1 mmol) of diethyl azodicarboxylate 40% toluene solution (DEAD) was slowly dropwise added over a period of 10 minutes. Then, after returning the system to room temperature, stirring was carried out for 6 hours, and then water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:6), followed by recrystallization by using dichloromethane and hexane (100 mL of hexane was heated to 55° C., and dichloromethane was added until the solid dissolved), to obtain 1.1 g of white solid compound A. The yield was 62%.

1H-NMR spectrum of compound A (solvent: CDCl$_3$, internal standard: TMS) was δ(ppm): 4.24 (2H, t), 4.52 (2H, t), 5.84-6.46 (3H, m), 6.93-6.95 (2H, d), 7.38-7.56 (17H, m). The melting point of the obtained compound A was 105° C.

Example 2

In the step of preparing compound A from compound A-3, as described in Example 1, instead of 2-hydroxyethyl acrylate, 4-hydroxy-butyl acrylate was used to obtain compound B. The yield was 58%.

(B)

1H-NMR spectrum of compound B (solvent: CDCl$_3$, internal standard: TMS) was δ(ppm): 1.85-1.9 (4H, m), 4.02 (2H, t), 4.24 (2H, t), 5.80-6.42 (3H, m), 6.90-6.92 (2H, d), 7.35-7.56 (17H, m). The melting point of the obtained compound B was 117° C.

Example 3

Compound C was prepared via compounds C-1 and C-2 in accordance with the following methods.

(C-3)

In the formulae, TIPS represents a triisopropylsilyl group.

(a) Preparation of Compound C-1

In 100 mL of THF, 12 g (30 mmol) of compound A-1 obtained as described above, was dissolved and stirred at −30° C. in a nitrogen atmosphere. Then, 12 mL (30 mmol) of a hexane solution of n-butyllithium having a concentration of 2.6 mol/L was slowly dropwise added over a period of about 5 minutes. After a reaction at −30° C. for 20 minutes, 3.9 mL (15 mmol) of diphenyldichlorosilane diluted with 30 mL of THF was slowly dropwise added over a period of about 15 minutes. After maintaining the system at −30° C. for 15 minutes, a reaction was carried out at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:15), to obtain 6.0 g of white solid compound C-1. The yield was 59%.

(b) Preparation of Compound C-2

To 100 mL of THF, 1.5 g (2.2 mmol) of compound C-1 and 1.3 g (4.9 mmol) of tetrabutylammonium fluoride (TBAF) were dissolved and stirred at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:1), to obtain 0.7 g of white solid compound C-2 The yield was 85%.

(c) Preparation of Compound C

To 100 mL of THF, 0.7 g (1.9 mmol) of compound C-2, 1.1 g (4.1 mmol) of triphenylphosphine and 0.59 g (4.1 mmol) of 2-hydroxyethyl acrylate were dissolved and stirred, and while cooling by an ice bath in a nitrogen atmosphere, 1.8 g (4.1 mmol) of diethyl azodicarboxylate 40% toluene solution (DEAD) was slowly dropwise added over a period of 10 minutes. The system was returned to room temperature, and stirring was carried out for 6 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:4), followed by recrystallization by using dichloromethane and hexane (100 mL of hexane was heated to 55° C., and dichloromethane was added until the solid dissolved), to obtain 1.1 g of white solid compound C. The yield was 62%.

1H-NMR spectrum of compound C (solvent: CDCl$_3$, internal standard: TMS) was δ(ppm): 4.23 (4H, t), 4.52 (4H, t), 5.84-6.47 (6H, m), 6.93-6.95 (4H, d), 7.36-7.55 (14H, m).

The melting point of the obtained compound C was 80° C.

Example 4

Compound D was prepared via compound D-1 in accordance with the following methods.

(a) Preparation of Compound D-1

6 g (63 mmol) of 1,3,5-trihydroxybenzene, 8.3 g (32 mmol) of triphenylphosphine and 3.7 g (32 mmol) of 2-hydroxyethyl acrylate were dissolved in 400 mL of THF, and while cooling by an ice bath in a nitrogen atmosphere, 14 g (32 mmol) of diethyl azodicarboxylate 40% toluene solution (DEAD) was slowly dropwise added over a period of 20 minutes. After the dropwise addition, a reaction was carried out at room temperature for 15 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:1), to obtain 1.4 g of white solid compound D-1. The yield was 9.1%.

(b) Preparation of Compound D

1.4 g (4.3 mmol) of compound D-1 and 0.6 mL (4.3 mmol) of triethylamine were dissolved in 50 mL of THF, and while cooling by an ice bath in a nitrogen atmosphere, 1.3 g (4.3 mmol) of chlorotriphenylsilane diluted with 30 mL of THF was slowly dropwise added over a period of 10 minutes. After the dropwise addition, a reaction was carried out at room temperature for 15 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:4), to obtain 0.90 g of colorless transparent highly viscous compound D. The yield was 42%.

1H-NMR spectrum of compound D (solvent: CDCl$_3$, internal standard: TMS) was δ(ppm): 3.94 (4H, t), 4.37 (4H, t), 5.83-6.44 (9H, m), 7.37-7.68 (15H, m).

Example 5

Compound E was prepared via compound E-1 in accordance with the following methods.

In the above formulae, TBDMS represents a tert-butyldimethylsilyl group.

(a) Preparation of Compound E-1

5.0 g (25 mmol) of 2-(4-bromophenyl)ethyl alcohol and 5.6 g (37 mmol) of tert-butyldimethylchlorosilane (TBDMS-Cl) were dissolved in 200 mL of THF, and to the obtained solution, 4.1 mL (30 mmol) of triethylamine was dropwise added in a nitrogen atmosphere. After the dropwise addition, a reaction was carried out at room temperature for 15 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:19), to obtain 6.4 g of colorless transparent compound E-1. The yield was 82%.

(b) Preparation of Compound E-2

To 100 mL of THF, 5.0 g (16 mmol) of compound E-1 was dissolved and stirred at −30° C. in a nitrogen atmosphere. Then, 10 mL (16 mmol) of a n-butyllithium hexane solution having a concentration of 1.6 mol/L was slowly dropwise added over a period of about 5 minutes. After a reaction at −30° C. for 20 minutes, 5.1 g (17 mmol) of triphenylchlorosilane dissolved in 50 mL of THF was slowly dropwise added over a period of about 15 minutes. Then, after maintaining the system at −30° C. for 15 minutes, a reaction was carried out at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:19), to obtain 5.2 g of transparent colorless compound E-2. The yield was 66%.

(c) Preparation of Compound E-3

To 100 mL of THF, 5.2 g (11 mmol) of compound E-2 and 3.0 g (11 mmol) of tetrabutylammonium fluoride (TBAF) were dissolved and stirred at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:2), to obtain 2.8 g of white solid compound E-3. The yield was 70%.

(c) Preparation of Compound E 2.8 g (7.3 mmol) of compound E-3 and 1.1 mL (8.0 mmol) of triethylamine were dissolved in 200 mL of THF, followed by stirring in an ice bath in a nitrogen atmosphere. Then, 0.65 mL (8.0 mmol) of acrylic acid chloride diluted with 10 mL of THF, was slowly dropwise added over a period of about 10 minutes and then stirred at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:6), to obtain 1.5 g of white solid compound E. The yield was 47%.

1H-NMR spectrum of compound E (solvent: $CDCl_3$, internal standard: TMS) was δ(ppm): 3.00 (2H, t), 4.39 (2H, t), 5.80-6.41 (3H, m), 7.23-7.57 (19H, m). The melting point of the obtained compound E was 124° C.

Example 6

Compound F was prepared via compound F-1 in accordance with the following methods.

(F)

(F-3)

(F-4)

(F)

In the above formulae, THP represents a 2-tetrahydropyranyl group.

(a) Preparation of Compound F-1

15 g (41 mmol) of 2,2,3,3,4,4,5,5,6,6,7,7-dodecafluoro-1,8-octanediol and 3.7 mL (41 mmol) of 3,4-dihydro-2H-pyran (DHP) were dissolved in 350 mL of THF, and further, 0.50 g (2.9 mmol) of p-toluenesulfonic acid monohydrate (PTS) was introduced, followed by a reaction at room temperature for 5 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:7), to obtain 9.0 g of colorless transparent compound F-1. The yield was 49%.

(b) Preparation of Compound F-2

9.0 g (20 mmol) of compound F-1 and 3.1 mL (22 mmol) of triethylamine were dissolved in 200 mL of THF, and then 4.0 mL (22 mmol) of perfluorobutanesulfonyl fluoride was introduced, followed by a reaction at room temperature for 5 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:6), to obtain 14 g of colorless transparent compound F-2. The yield was 95%.

(c) Preparation of Compound F-3

6.6 g (19 mmol) of compound A-3 obtained as described above, 14 g (18 mmol) of compound F-2, 13 g (94 mmol) of potassium carbonate and 0.5 g (3.0 mmol) of potassium iodide were added to a mixed solution comprising 300 mL of acetone and 100 mL of N,N-dimethylformamide, followed by heating and stirring for 10 hours at 60° C. After returning the system to room temperature, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:9), to obtain 11 g of white solid compound F-3. The yield was 75%.

(d) Preparation of Compound F-4

11 g (14 mmol) of compound F-3 was dissolved in 100 mL of THF and 100 mL of ethanol, and 0.30 g (1.7 mmol) of p-toluenesulfonic acid monohydrate (PTS) was introduced, followed by a reaction at room temperature for 5 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:3), to obtain 9.5 g of white solid compound F-4. The yield was 98%.

(e) Preparation of Compound F 9.5 g (14 mmol) of compound F-4 and 2.0 mL (14 mmol) of triethylamine were dissolved in 300 mL of THF, followed by stirring in an ice bath in a nitrogen atmosphere. Then, 1.2 mL (15 mmol) of acrylic acid chloride diluted with 10 mL of THF, was slowly dropwise added over a period of about 10 minutes and then stirred at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:8), to obtain 7.6 g of white solid compound F. The yield was 74%.

1H-NMR spectrum of compound F (solvent: CDCl$_3$, internal standard: TMS) was δ(ppm): 4.48 (2H, t), 4.67 (2H, t), 5.97-6.54 (3H, m), 6.98 (2H, d), 7.23-7.59 (17H, m). The melting point of the obtained compound F was 68° C.

Example 7

Compound G was prepared via compound G-1 in accordance with the following methods.

(G)

In the above formulae, THP represents a 2-tetrahydropyranyl group.

(a) Preparation of Compound G-1

9.0 g (42 mmol) of 2,2,3,3,4,4-hexafluoro-1,5-pentanediol and 3.6 mL (42 mmol) of 3,4-dihydro-2H-pyran (DHP) were dissolved in 350 mL of THF, and 0.50 g (2.9 mmol) of p-toluenesulfonic acid monohydrate (PTS) was introduced, followed by a reaction at room temperature for 5 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:6), to obtain 5.9 g of colorless transparent compound G-1. The yield was 47%.

(b) Preparation of Compound G-2

5.9 g (20 mmol) of compound G-1 and 3.1 mL (22 mmol) of triethylamine were dissolved in 200 mL of THF, and then 4.0 mL (22 mmol) of perfluorobutanesulfonyl fluoride was introduced, followed by a reaction at room temperature for 5 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:7), to obtain 9.5 g of colorless transparent compound G-2. The yield was 82%.

(c) Preparation of Compound G-3

2.0 g (5.6 mmol) of compound A-3 obtained as described above, 3.6 g (6.3 mmol) of compound G-2, 3.9 g (28 mmol) of potassium carbonate and 0.2 g (1.2 mmol) potassium iodide were added to a mixed solution comprising 100 mL of acetone and 50 mL of N,N-dimethylformamide, followed by heating and stirring for 10 hours at 60° C. After returning the system to room temperature, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:9), to obtain 2.9 g of white solid compound G-3. The yield was 80%.

(d) Preparation of Compound G-4

2.9 g (4.5 mmol) of compound G-3 was dissolved in 50 mL of THF and 50 mL of ethanol, and 0.20 g (1.1 mmol) of p-toluenesulfonic acid monohydrate (PTS) was further introduced, followed by a reaction at room temperature for 5 hours. Then, water and ethyl acetate were added, and the organic layer was extracted. The organic layer was sufficiently dried by adding magnesium sulfate, and then, the solvent was distilled off. Then, purification was carried out by column chromatography employing ethyl acetate and hexane (volume ratio of 1:3), to obtain 2.2 g of white solid compound G-4. The yield was 90%.

(e) Preparation of Compound G 2.2 g (4.0 mmol) of compound G-4 and 0.61 mL (4.4 mmol) of triethylamine were dissolved in 100 mL of THF, followed by stirring in an ice bath in a nitrogen atmosphere. Then, 0.35 mL (4.4 mmol) of acrylic acid chloride diluted with 10 mL of THF, was slowly dropwise added over a period of about 10 minutes and then stirred at room temperature for 3 hours. Then, water and ethyl acetate were added, and the organic layer was extracted. The organic layer was sufficiently dried by adding magnesium sulfate, and then, the solvent was distilled off. Purification was carried out by column chromatography employing ethyl acetate and hexane (volume ratio of 1:8), to obtain 1.6 g of white solid compound G. The yield was 66%.

1H-NMR spectrum of compound G (solvent: $CDCl_3$, internal standard: TMS) was δ(ppm): 4.47 (2H, t), 4.68 (2H, t), 5.95-6.54 (3H, m), 6.98 (2H, d), 7.22-7.59 (17H, m). The melting point of the obtained compound G was 77° C.

<Polymerization of Photocurable Composition, and Evaluation of Refractive Index>

Example 8

To 100 parts by weight of compound A, 0.5 part by weight of "IC184" (tradename) manufactured by Ciba Specialty Chemicals was added as a photo-initiator, followed by stirring under heating until the mixture became uniform thereby to obtain a liquid composition. A pair of glass plates were bonded at four corner portions by an adhesive having glass beads with a diameter of 10 μm mixed, to prepare a glass cell with a glass distance of 10 μm. The above composition was injected in the liquid state into this glass cell, and then, to the glass plates, ultraviolet rays were applied from a perpendicular direction for 2 minutes. The illuminance of a high pressure mercury lamp employed was 50 mW/cm$^2$ with a wavelength of 365 nm.

Thereafter, one of the pair of glass plates was removed to obtain a test specimen A having the cured resin attached on one side. Using a prism coupler ("Model 2010", manufactured by Metricon), the refractive index at a wavelength of 633 nm was measured at room temperature and found to be 1.618, and thus it was confirmed to be a cured resin having a high refractive index. In the same manner, the refractive indices at 404 nm and 791 nm were measured, and based on the measured three values, parameters A, B and C of the Cauchy's dispersion formula $(n(\lambda)=A+B/\lambda^2+C/\lambda^4)$ were obtained from fitting by means of a least square method, whereby refractive indices at from 400 nm to 800 were led, and based thereon, the Abbe number (vd) was calculated, whereby the Abbe number (vd) was found to be 26.4.

Examples 9 to 14

Test specimens B, C, D, E, F and G were prepared in the same manner as in Example 8 except that instead of compound A, compounds B, C, D, E, F and G were used. The refractive indices of the test specimens B, C, D, E, F and G at a wavelength of 633 nm were measured at room temperature and found to be 1.611, 1.605, 1.595, 1.621, 1.525 and 1.565, respectively, and thus, they were confirmed to be resins having high refractive indices. Further, the Abbe numbers were obtained in the same manner as in Example 8 and found to be 27.2, 27.8, 29.1, 26.8, 31.3 and 35.0, respectively.

<Polymerization of Photocurable Composition and Evaluation of Light Resistance>

Example 15

A glass cell was prepared in the same manner as in Example 8 except that glass plates each having an antireflective film coating on one surface, were used, so that the surfaces opposite to the coating surfaces face each other. To 100 parts by weight of compound A, 0.5 part by weight of "IC184" (tradename) manufactured by Ciba Specialty Chemicals was added as a photoinitiator, followed by stirring under heating until the mixture became uniform to obtain a liquid composition. The obtained liquid composition was injected in the liquid state into the glass cell, and ultraviolet rays were applied for 2 minutes from a perpendicular direction to the glass plates to obtain a laminate A. Here, the illuminance of the high pressure mercury lamp employed, was 50 mW/cm$^2$ at a wavelength of 365 nm.

The above laminate A was irradiated with 50 kJ/mm$^2$ of blue LD light with oscillation wavelength of 406 nm at 80° C. The transmittances were measured before and after the irradiation, whereby the transmittance change $\Delta T_{LD}$ was less than 1%. Here, $\Delta T_{LD}$=(blue LD light transmittance before irradiation)−(blue LD light transmittance after irradiation). Further, $\Delta T_{LD}$ after repeating irradiation with blue LD light in the same manner continuously till a total of 180 kJ/mm$^2$, was 5.1%.

Example 16

Laminate E was prepared in the same manner as in Example 15 except that compound E was used instead of compound A. The light resistance test was carried out in the same manner as in Example 15, and the transmittance change of the laminate E was measured, whereby $\Delta T_{LD}$ was less than 1%. Further, $\Delta T_{LD}$ after repeating irradiation with blue LD light in the same manner continuously till a total of 180 kJ/mm$^2$, was less than 1%.

Example 17

The laminate A obtained in Example 15 was irradiated with ultraviolet rays (high pressure mercury lamp) in a perpendicular direction to the glass plates at room temperature for 2 minutes. The integral quantity of light by the high pressure mercury lamp employed was 6 J/cm$^2$ at a wavelength of 365 nm. The transmittance at a wavelength of 400 nm was measured by a spectral photometer (U-3310, manufactured by Hitachi High-Technologies Corporation), whereby the transmittance change $\Delta T_{UV}$ before and after the irradiation was less than 1%. Here, $\Delta T_{UV}$=(light transmittance before irradiation)−(light transmittance after irradiation).

Example 18

Laminates B, C, D, F and G were prepared in the same manner as in Example 15 except that instead of compound A, compounds B, C, D, F and G were used. In the same manner as in Example 17, the transmittances of the laminates B, C, D, E, F and G were measured, whereby in each case, $\Delta T_{UV}$ was less than 1%.

Comparative Example 1

A cured resin was prepared in the same manner as in Example 8 except that instead of compound A, the following compound H was used. The refractive index at a wavelength of 633 nm was measured at room temperature and found to be 1.603.

(H)

Laminate H was prepared in the same manner as in Example 15 except that instead of compound A, compound H was used. Then, in the same manner as in Example 15, the transmittance of the laminate H was measured, whereby $\Delta T_{PD}$ was 58.5%.

Further, in the same manner as in Example 17, the transmittance of the laminate H was measured whereby $\Delta T_{UV}$ was 7.1%.

Comparative Example 2

A cured resin was prepared in the same manner as in Example 8 except that instead of compound A, the following compound I was used. The refractive index at a wavelength of 633 nm was measured at room temperature and found to be 1.623.

(I)

Laminate I was prepared in the same manner as in Example 15 except that instead of compound A, compound I was used. Then, in the same manner as in Example 15, the transmittance of the laminate I was measured, whereby $\Delta T_{PD}$ was 50.0%.

Further, in the same manner as in Example 17, the transmittance of the laminate I was measured, whereby $\Delta T_{UV}$ was 2.6%.

Table 1 shows the evaluation results in Examples 8 to 14 and Comparative Examples 1 and 2. As is evident from this Table, the resin materials obtainable by using the polymerizable compounds of the present invention are excellent in light resistance, while realizing high refractive indices equivalent to conventional materials.

In Table 1, "-" means that the measurement or evaluation was not carried out.

TABLE 1

|  | Compound | Refractive index of resin (wavelength: 33 nm) | Abbe number of resin νd | Transmittance change (before and after irradiation) | |
|---|---|---|---|---|---|
|  |  |  |  | $\Delta T_{LD}$ | $\Delta T_{UV}$ |
| Example 8 | Compound A | 1.618 | 26.4 | <1% | <1% |
| Example 9 | Compound B | 1.611 | 27.2 | — | <1% |
| Example 10 | Compound C | 1.605 | 27.8 | — | <1% |
| Example 11 | Compound D | 1.595 | 29.1 | — | <1% |
| Example 12 | Compound E | 1.621 | 26.8 | <1% | <1% |
| Example 13 | Compound F | 1.525 | 31.3 | — | <1% |
| Example 14 | Compound G | 1.565 | 35.0 | — | <1% |
| Comparative Example 1 | Compound H | 1.603 | 28.2 | 58.5% | 7.1% |
| Comparative Example 2 | Compound I | 1.623 | 24.1 | 50.0% | 2.6% |

INDUSTRIAL APPLICABILITY

A resin material obtainable from a photocurable composition containing the polymerizable compound of the present invention has a high refractive index and is useful for various optical applications. Particularly, it has high light resistance against blue light, and it can be used suitably for applications where a high refractive index material is required, such as optical disks or optical elements employing strong blue light.

The entire disclosure of Japanese Patent Application No. 2008-130155 filed on May 16, 2008 including specification, claims, drawings and summary is incorporated herein by reference in its entirety.

MEANING OF SYMBOLS

1, 13: Wavelength-selective diffraction grating
2, 3: Transparent substrate
4: Convexoconcave section
5: Filling section
11: Optical head device
12: Light source
14: Beam splitter
15: Collimator lens
16: Optical disk
17: Recording layer
18: Object lens
19: Light detector

What is claimed is:

1. A polymerizable compound represented by the following formula (1), wherein silicon and four cyclic groups are bonded directly or via oxygen:

(1)

in the formula (1), each of $A^1$, $A^2$, $A^3$ and $A^4$ which are independent of one another, is $—(O)_m—X$;

each of four m's which are independent of one another, is 0 or 1; and each of four X's which are independent of one another, is any cyclic group selected from a phenyl group, a cyclohexyl group, a cyclohexylphenyl group and a phenylcyclohexyl group; and from 1 to 4 hydrogen atoms in total in cyclic groups in $A^1$ to $A^4$ are substituted by a substituent represented by the following formula (2), and some or all of remaining hydrogen atoms in each of cyclic groups in $A^1$ to $A^4$ may be substituted by a methyl group, a methoxy group, a fluorine atom, a trifluoromethyl group or a trifluoromethoxy group:

$$CH_2=CR—COO—Y— \qquad (2)$$

in the formula (2), R is a hydrogen atom or a methyl group; and

Y is a single bond or an alkylene group; and some or all of hydrogen atoms in the alkylene group may be substituted by a fluorine atom, and the alkylene group may have an oxygen atom in a carbon-carbon bond adjacent thereto or at its terminal bonded to a cyclic group.

2. The polymerizable compound according to claim 1, wherein X is a phenyl group which may have a substituent.

3. The polymerizable compound according to claim 1, wherein Y is a $C_{2-12}$ alkylene or $C_{2-12}$ alkyleneoxy group, in which some or all of hydrogen atoms may be substituted by a fluorine atom.

4. The polymerizable compound according to claim 3, wherein Y is a $C_{2-12}$ alkylene group.

5. The polymerizable compound according to claim 3, wherein Y is a $C_{2-12}$ alkyleneoxy group.

6. The polymerizable compound according to claim 1, wherein the sum in number of substituents represented by the formula (2) in the compound represented by the formula (1) is 1 or 2.

7. The polymerizable compound according to claim 1, wherein in each of $A^1$ to $A^4$, the cyclic group is a phenyl group which may have a substituent, and m is 0.

8. A photocurable composition containing the polymerizable compound as defined in claim 1.

9. An optical element using a resin material obtained by curing the photocurable composition as defined in claim 8.

10. An optical head device using the optical element as defined in claim 9.

* * * * *